US00PP32255P3

(12) United States Plant Patent
Rattanasophon

(10) Patent No.: US PP32,255 P3
(45) Date of Patent: Sep. 29, 2020

(54) ***CURCUMA* PLANT NAMED 'CPH MAGENTA'**

(50) Latin Name: ***Curcuma* hybrid**
Varietal Denomination: CPH Magenta

(71) Applicant: Chiangmai Plants and Herbs Co., Ltd., Chiangmai (TH)

(72) Inventor: Sasirin Rattanasophon, Chiangmai (TH)

(73) Assignee: Chiangmai Plants and Herbs Co., Ltd., Chiangmai (TH)

( * ) Notice: Subject to any disclaimer, the term of this patent is extended or adjusted under 35 U.S.C. 154(b) by 0 days.

(21) Appl. No.: 16/501,640

(22) Filed: May 15, 2019

(65) Prior Publication Data

US 2019/0357406 P1 Nov. 21, 2019

Related U.S. Application Data

(60) Provisional application No. 62/762,738, filed on May 17, 2018.

(51) Int. Cl.
*A01H 5/02* (2018.01)
*A01H 6/00* (2018.01)

(52) U.S. Cl.
USPC ..... Plt./421
CPC ..... *A01H 6/00* (2018.05); *A01H 5/02* (2013.01)

(58) Field of Classification Search
USPC ..... Plt./421
See application file for complete search history.

*Primary Examiner* — Susan McCormick Ewoldt
(74) *Attorney, Agent, or Firm* — The Webb Law Firm

(57) ABSTRACT

A new and distinct *curcuma* plant having magenta colored inflorescences.

1 Drawing Sheet

Botanical classification: *Curcuma* hybrid.
Varietal denomination: 'CPH Magenta'.

BACKGROUND OF THE INVENTION

The present invention comprises a new and distinct variety of *curcuma* plant known by the varietal name 'CPH Magenta' (previously referred to in U.S. Provisional Patent Application No. 62/762,738 as simply "Magenta"). The new variety was discovered in 2017 in Chiangmai, Thailand as the result of a planned breeding program with the purposes of providing *curcuma* plants with new coloration and characteristics. The new variety is the result of a cross between an unnamed and unpatented *Curcuma alismatifolia* variety (female parent) and an unnamed and unpatented *Curcuma aurantiaca* variety (male parent). The new variety is similar in upper inflorescence leaf position to its female parent, but 'CPH Magenta' differs in lower inflorescence bract color (dark brown-purple for 'CPH Magenta' compared to green for its female parent) and overall inflorescence shape to its female parent. 'CPH Magenta' exhibits similar inflorescence shape and bract colors to its male parent, but has smaller inflorescences than its male parent. Tissue culture and bulb asexual reproductions of the new variety first occurred in 2017 in Chiangmai, Thailand. 'CPH Magenta' has been trial and field tested and has been found to retain its distinctive characteristics and remain true to type through successive propagations. The present invention has not been evaluated under all possible environmental conditions. The phenotype may vary with variations in environment without a change in the genotype of the plant.

The inflorescence color and shape distinguish 'CPH Magenta' from other *curcuma* varieties known to the breeder. Further, when 'CPH Magenta' is compared to *Curcuma* hybrid 'CPH Orange' (U.S. Plant patent application Ser. No. 16/501,639), the varieties are similar in exhibiting a red upper surface leaf midrib. However, the varieties differ in inflorescence color ('CPH Orange' has orange colored inflorescences) and plant height.

DESCRIPTION OF THE DRAWING

The accompanying photographic drawing taken at approximately 60 days of age illustrates the new variety, with the colors being as nearly true as is possible with color illustrations of this type.

DESCRIPTION OF THE PLANT

The following detailed description sets forth the characteristics of the new variety at approximately 60 days of age. The data which defines these characteristics was collected under natural light in Chiangmai, Thailand. Plants of the new variety were grown in 20.3 cm pots in a plastic greenhouse in Chiangmai, Thailand and watered 1-2 times a day, if needed. Color references are primarily to the 2016 HTML Color Chart and The 2015 R.H.S. Colour Chart of The Royal Horticultural Society of London, 6th Edition, except where general color terms are used.

PLANT

Time to initiate roots: About 20-30 days at about 30-33° C.
Time to produce a rooted young plant: About 45 days at about 30-33° C.
Root description: Fibrous, with a pale yellow colored (FAFCF5) milk tank.
Number of rhizomes produced per plant: From 1-3.
Rhizome diameter: 3.0-4.0 cm.
Growth habit: Annual.
Plant height (soil level to top of inflorescences): 50.0 cm.
Plant diameter: 30.0 cm.

Pubescence: Lightly present on bracts and leaves.
Disease resistance/susceptibility: None observed.
Pest resistance/susceptibility: None observed.
Temperature tolerance: 20-40° C. or tropical climate conditions.
Drought tolerance: Unknown.
Seed/fruit: None observed to date.
Leaves:
Arrangement.—Alternate.
*Average number per plant*.—From 3-5.
*Length*.—30.0 cm.
*Width*.—8.0 cm.
*Shape of leaf* (*generally*).—Linear elliptic.
*Shape of apex*.—Attenuate.
*Shape of base*.—Obtuse.
*Margin description*.—Entire.
*Texture*.—Upper surface: Smooth. Lower surface: Pubescence present.
*Aspect*.—Upright.
*Color*.—Young leaves: Upper surface: Light green (74AF1B). Lower surface: Light green (74AF1B). Mature leaves: Upper surface: Green (96B365). Lower surface: Green (96B365).
*Veins*.—Appearance: Pinnate and penninerved. Color: Upper surface: Green (3E5D19) with a red (807976) midrib. Lower surface: Green (3E5D19).
*Leaf sheaths*.—Length: 10.0-20.0 cm. Width: 2.0 cm. Texture: Upper surface: Smooth. Lower surface: Smooth. Color: Upper surface: RHS 142A. Lower surface: RHS 142A. Venation: Pattern: Parallel. Color: RHS 183A.

INFLORESCENCE

Inflorescence arrangement: 1 compact inflorescence per shoot.
Inflorescence number per plant: From 1-3.
Inflorescence length: 20.0 cm.
Inflorescence diameter: 8.0 cm.
Fragrance: None.
Flower bracts:
*Total number per inflorescence*.—Approximately 20.
*Upper bracts*.—Number: Approximately 10. Length: 4.0 cm. Width: 3.0 cm. Shape: Oblanceolate. Apex: Acute. Base: Shallow U-shaped. Margin: Entire. Texture: Upper surface: Smooth. Lower surface: Smooth. Color: Upper surface: Magenta RHS 71A. Lower surface: Magenta RHS 71A.
*Lower bracts*.—Number: Approximately 10. Length: 3.0-5.0 cm. Width: 3.0-5.0 cm. Shape: Obovate. Apex: Mucronate. Base: Reverse omega-shaped. Margin: Entire. Texture: Upper surface: Smooth. Lower surface: Smooth. Color: Upper surface: Red (942627). Lower surface: Red (6C2827).

Flowers:
*Number per inflorescence*.—Approximately 50.
*Continuity of flowering*.—1 month.
*Lastingness of an individual flower*.—1-2 days.
*Length*.—Approximately 2.0 cm.
*Diameter*.—3.0 cm.
*Appearance*.—Orchidaceous form.
*Upper petals*.—Upper surface color: Yellow (A66E2E). Lower surface color: Yellow (A66E2E).
*Lower petals*.—Upper surface color: Purple (A86078). Lower surface color: Purple (A86078).
*Flower buds*.—Length: 5.0 cm. Diameter: 2.0 cm. Shape: Round apex, with the base connected in a cone shape. Texture: Smooth. Color: RHS 10C and 84D, with RHS 71B at the tip.
*Sepals*.—Number: 3. Calyx arrangement: In overlapping circles. Length: 1.0 cm. Width: 0.5 cm. Overall shape: Elliptic. Apex: Elliptic. Base: Connected in a cone shape. Texture: Smooth (both surfaces). Color: Upper surface: RHS 71B. Lower surface: RHS 10C.
Peduncles:
*Length*.—20.0 cm.
*Diameter*.—1.0 cm.
*Texture*.—Smooth.
*Angle*.—Upright.
*Color*.—Green (827912).

REPRODUCTIVE ORGANS

Stamens:
*Number*.—1.
Filament:
*Length*.—2.0 cm.
*Diameter*.—1.0 mm.
*Color*.—Pale cream (C6AE98).
Anthers:
*Shape*.—2-lobed.
*Length*.—3.0 mm.
*Color*.—Pale cream (C6AE98).
Pollen: None observed.
Pistils:
*Number*.—1.
*Length*.—1.0 cm.
Style:
*Length*.—1.0 cm.
*Diameter*.—2.0 mm.
*Color*.—Pale cream (C6AE98).
Stigma:
*Length*.—2.0 mm.
*Diameter*.—2.0 mm.
*Color*.—Pale cream (C6AE98).

I claim:

1. A new and distinct variety of *curcuma* plant, as is herein illustrated and described.

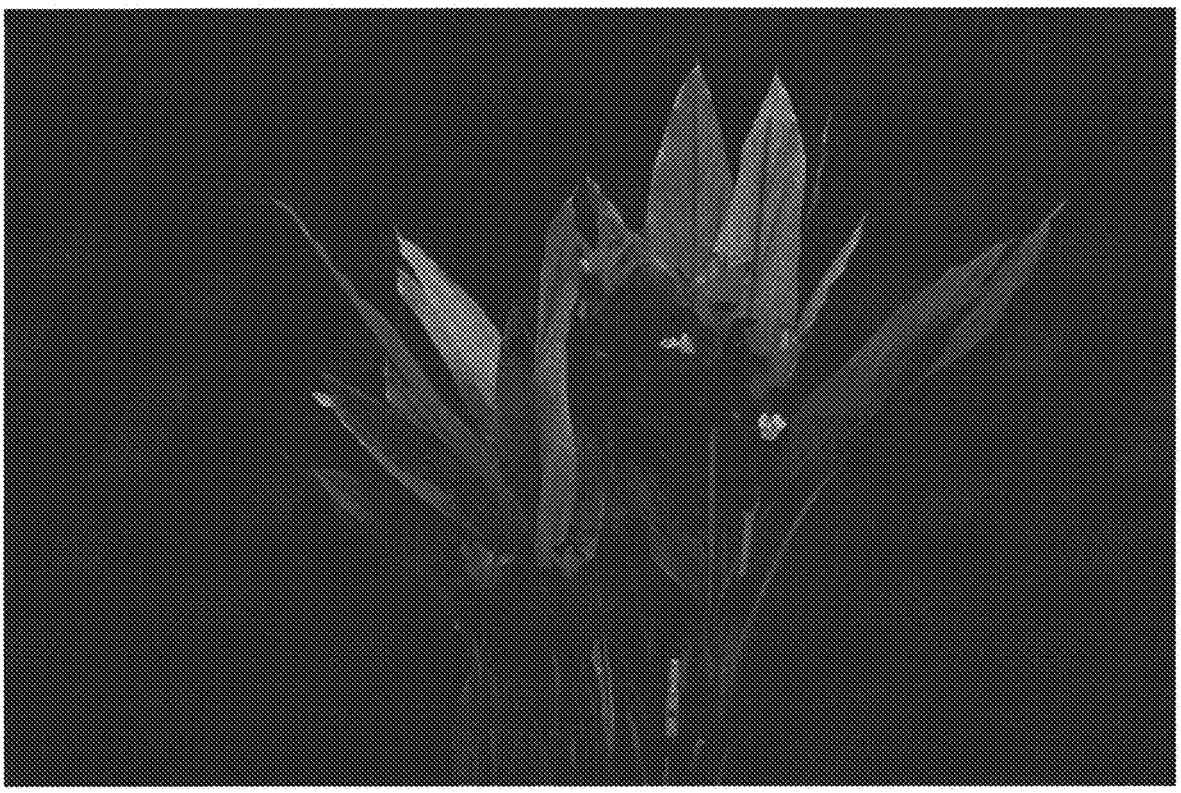

* * * * *